United States Patent [19]
Markowitz

[11] Patent Number: 6,099,315
[45] Date of Patent: Aug. 8, 2000

[54] APPLICATOR TIP FOR DESENSITIZING AGENTS AND METHOD

[75] Inventor: Kenneth Markowitz, Fanwood, N.J.

[73] Assignee: Block Drug Company, Inc., Jersey City, N.J.

[21] Appl. No.: 08/530,817

[22] Filed: Sep. 20, 1996

[51] Int. Cl.[7] .................................................. A61C 5/00
[52] U.S. Cl. ................................. 433/215; 433/141
[58] Field of Search .................... 433/80, 164, 141, 433/215, 217.1; 601/141, 139, 140; 132/309, 310, 311; 15/110

[56] References Cited

U.S. PATENT DOCUMENTS

| | | |
|---|---|---|
| D. 121,506 | 7/1940 | Davis . |
| 140,429 | 7/1873 | O'Donoghue . |
| 1,248,675 | 12/1917 | Kowinsky . |
| 1,691,863 | 11/1928 | Van Sant ................................... 15/110 |
| 1,935,099 | 11/1933 | O'Donnell ............................. 601/141 |
| 1,996,205 | 4/1935 | Jackson . |
| 2,110,315 | 3/1938 | Wolfson ................................... 128/62 |
| 2,164,219 | 6/1939 | McGerry ................................. 601/141 |
| 2,279,355 | 4/1942 | Wilensky ................................. 15/110 |
| 2,512,059 | 6/1950 | Haeusser ................................. 601/141 |
| 2,614,556 | 10/1952 | Staunt ..................................... 601/141 |
| 2,684,603 | 7/1954 | Bileth ..................................... 601/141 |
| 4,486,109 | 12/1984 | Rosofsky ................................ 601/141 |
| 4,543,679 | 10/1985 | Rasofsky et al. ........................ 15/110 |
| 4,586,901 | 5/1986 | Tanaka et al. ........................... 433/147 |
| 4,672,986 | 6/1987 | Hadary ................................... 132/309 |
| 5,044,356 | 9/1991 | Fishman et al. ......................... 433/80 |
| 5,205,302 | 4/1993 | Lemon et al. .......................... 132/321 |
| 5,358,404 | 10/1994 | Schumacher ........................... 433/164 |
| 5,449,509 | 9/1995 | Jackson et al. .......................... 424/49 |
| 5,486,350 | 1/1996 | Norfleet et al. .......................... 424/49 |
| 5,503,823 | 4/1996 | Norfleet et al. .......................... 424/52 |
| 5,505,933 | 4/1996 | Norfleet et al. .......................... 424/52 |

*Primary Examiner*—Cary E. O'Connor

[57] ABSTRACT

The present invention is a method for desensitizing and thereby relieving the pain and discomfort that often accompanies sensitive teeth in humans. A desensitizing agent in the form of a toothpaste, gel or mouthwash is applied to the surface of the teeth and physically forced into the dentinal tubules responsible for the sensitive condition using a flexible rubber or plastic applicator in the form of a cylindrical or rectangular post or block, preferably with an upper surface in the form of a recessed indentation, serrated surface or concave-shaped cup.

11 Claims, 5 Drawing Sheets

APPLICATOR TIP FOR DESENSITIZING AGENTS AND METHOD

FIELD OF THE INVENTION

The present invention relates generally to methods for the treatment of pain and discomfort associated with hypersensitive teeth. More particularly, the present invention relates to devices for the application of oral compositions that relieve the pain and discomfort associated with hypersensitive teeth.

BACKGROUND OF THE INVENTION

Dentin is a portion of the tooth internal to the enamel and cementum that has a radially striated appearance owing to a large number of fine canals or tubules known as the dentinal tubules. These run from the pulp cavity to the periphery of the dentin and are generally one to two microns in diameter at their base and somewhat narrower at their periphery.

Hypersensitive teeth is an irritating and painful condition caused by the existence of these hollow, dentin tubules that allow the nerves within the root canal and pulp of the tooth to be influenced by the external oral environment. Whereas the dentinal tubules are normally shielded from the external environment by the tooth enamel or cementum, the condition of tooth hypersensitivity arises when the enamel or cementum has eroded or recedes in areas on the tooth, particularly along the gum line, which directly exposes the tubules. Heat, cold, chemicals and physical or mechanical pressure or stimuli such as brushing all are able to irritate the nerve through the dentin tubules and thereby create the unpleasant sensation of pain. The pain of sensitive teeth results from these stimuli which cause fluid movements in the dentinal tubules that activate pulpal nerve endings. Such pain certainly does not encourage daily oral care and treatment and so as a result those plagued with hypersensitive teeth do not brush as often as they should nor can they always enjoy the food and beverages available in today's society.

Various attempts have been made in the art to cure or treat hypersensitive teeth so as to relieve the associated pain. U.S. Pat. No. 4,057,021 to Pashley et. al. teaches the desensitization of these teeth through the application of an alkali metal salt or ammonium oxalate to the surface of the tooth. U.S. Pat. Nos. 4,631,185 and 4,751,072 to Kim disclose the desensitization of teeth using oral compositions comprising potassium salts while U.S. Pat. No. 4,990,327 to Neirinchx describes the desensitization of teeth with strontium and fluoride ions. These chemicals act directly on the nerve endings within the tooth by somehow blocking the electrochemical impulses that are fired from one nerve cell to the next in the transmission of the pain signal. Other prior art methods disclose the treatment of hypersensitive teeth using zinc and strontium ions (U.S. Pat. No. 3,888,976 to Mlksey et. al.), chloride salts (U.S. Pat. No. 3,689,686 to Svajda) and apatite particles (U.S. Pat. Nos. 4,634,589 and 4,710,372 to Scheller). Although these chemical methods of treatment provide relief to some degree, they often require several weeks of application before they are effective.

Other methods have developed over the years which utilize various polymer systems for delivery of active agents to the teeth and gums. U.S. Pat. No. 4,685,883 to Jernberg discloses the use of biodegradable microsphere to deliver chemotherapeutic agents to lesions in the gums. U.S. Pat. No. 3,956,480 to Dichter et. al. describes and claims the treatment of teeth with anionic polymers that are complexed with a cationic antimicrobial agent such as chlorhexidine.

Along a similar vein U.S. Pat. Nos. 5,300,290 and 5,320,842 to J. Spencer disclose the use of solid polymeric particles such as polystyrene, polymethyl methacrylate, and polyvinyltoluene among others that have an ionically charged outer surface onto which an oppositely charged antimicrobial agent such as chlorhexidine is absorbed. The composition is used for antimicrobial action in the oral cavity in general and is not used in the treatment of hypersensitive teeth.

Two related patents disclose the use of similar microparticles for desensitizing teeth. U.S. Pat. Nos. 5,250,288 and 5,211,939 to Turetsky et. al. disclose a dentifrice comprising positively charged polystyrene particles which, it is postulated, desensitize the tooth by clinging to the surface of the teeth and block the dentin tubules thereby protecting the nerve from exposure to outside stimuli. The particles are generally from about 0.01 to 3.0 microns and may have an antimicrobial, analgesic or other therapeutic substance absorbed therein.

Finally, U.S. Pat. No. 5,270,031 to Lim et. al. discloses oral compositions for relieving the pain and discomfort caused by hypersensitive teeth consisting of water-soluble or water-swellable polyelectrolyte salts. The polyelectrolyte salts can comprise the anionic, cationic or amphoteric forms of methyl vinylether and maleic anhydride copolymers or polyacrylic acid polymers with sodium, calcium, potassium, ammonium, zinc and other similar metals.

However, in order for any of the aforementioned compositions to be effective in reducing the pain and discomfort of hypersensitive teeth, they must be able to enter the tubule for blockage thereof or to essentially anesthetize the nerve endings in the dentin pulp area. It has been shown that the tubules of sensitive human dentin may also contain organic material that prevents the bulk movement of certain materials into the tubules. Additionally, there is evidence that there is a continuous outward flow of fluid when vital dentin is exposed and the dentinal smear layer is removed. This outward fluid flow from the tubules would certainly counteract the ability of any desensitizing materials to enter the tubules for blockage or nerve anesthesia. The mere application of these materials with a toothbrush or paste or in solution as a mouthwash would not generate the sufficient driving force to cause the desensitizing materials to enter the tubules of live sensitive dentin. Hence, the need exists for a means to better apply a desensitizing composition to the tooth surface so as to insure tubule blockage and/or nerve anesthesia.

The prior art shows a number of auxiliary applicator type devices used in the cleaning or massaging of the teeth and gums. U.S. Pat. No. 1,248,675 to Kouinsky and U.S. Pat. No. 140,492 to O'Donoghue both disclose a tooth brush with two brush members located at opposite ends of the brush handle that are perpendicular to each other. One brush member is for brushing the teeth up and down while the other brushes from side to side. U.S. Pat. No. 2,110,315 to Wolfson discloses a toothbrush with a rubber serrated fusto-conical cup at the other end. The cup is used to massage the teeth and gums with a backward-forward motion of the serrated edges. U.S. Pat. No. 2,164,219 to McGerry discloses a toothbrush with distally mounted rubber cup members attached to the body of the handle by spring metal plates which urge the cups into crevices of the teeth as the device is moved over them during cleaning.

U.S. Pat. No. 4,543,679 to Rosofsky et. al. discloses a toothbrush assembly with a brush and oral hygiene device comprised of a porous material for the dispensing of an active agent on the teeth. This can then be rubbed over the teeth and a cleaning or antibacterial agent released thereon. Finally, U.S. Pat. No. 5,205,302 to Lemon discloses a toothbrush with a soft brush gum stimulator using a soft brush consisting of high density thin fibers. The stimulator may be shaped as a tapered pintle brush comprised of elongated center fibers or may be a cup-shaped brush, both of which are removable and replaceable from the end of the handle. In both cases the oral hygiene device is comprised of brush fibers for cleaning the interstitial space between the teeth.

SUMMARY OF THE INVENTION

The present invention comprises an improved method of applying desensitizing materials to the surface of hypersensitive teeth using a device that provides a positive inward directed pressure to the tooth surface so that the desensitizing particles are forced into the dentinal tubules responsible for the hypersensitivity.

DETAILED DESCRIPTION OF THE INVENTION

The applicator and method of the present invention provides an improved means for the administration of desensitizing agents beyond what is provided or made possible by a conventional toothbrush. The applicator and its method of use enhances the clinical desensitizing effect of desensitizing agents that act via the dentinal tubule blocking effect or nerve anesthesia. The teeth may be first brushed with a toothpaste composition containing a nerve desensitizing agent such as potassium nitrate which puts potassium in the tubules or some other desensitizing agent which is intended to desensitize by physically blocking the tubules. The applicator is then used to drive the blockage particles of toothpaste or mouthwash composition into the tubules for further pain relief. The desensitizing agent may also be applied directly to the surface of the tooth by placing some onto the applicator and then massaging it about the sensitive tooth surface.

Figure 1:
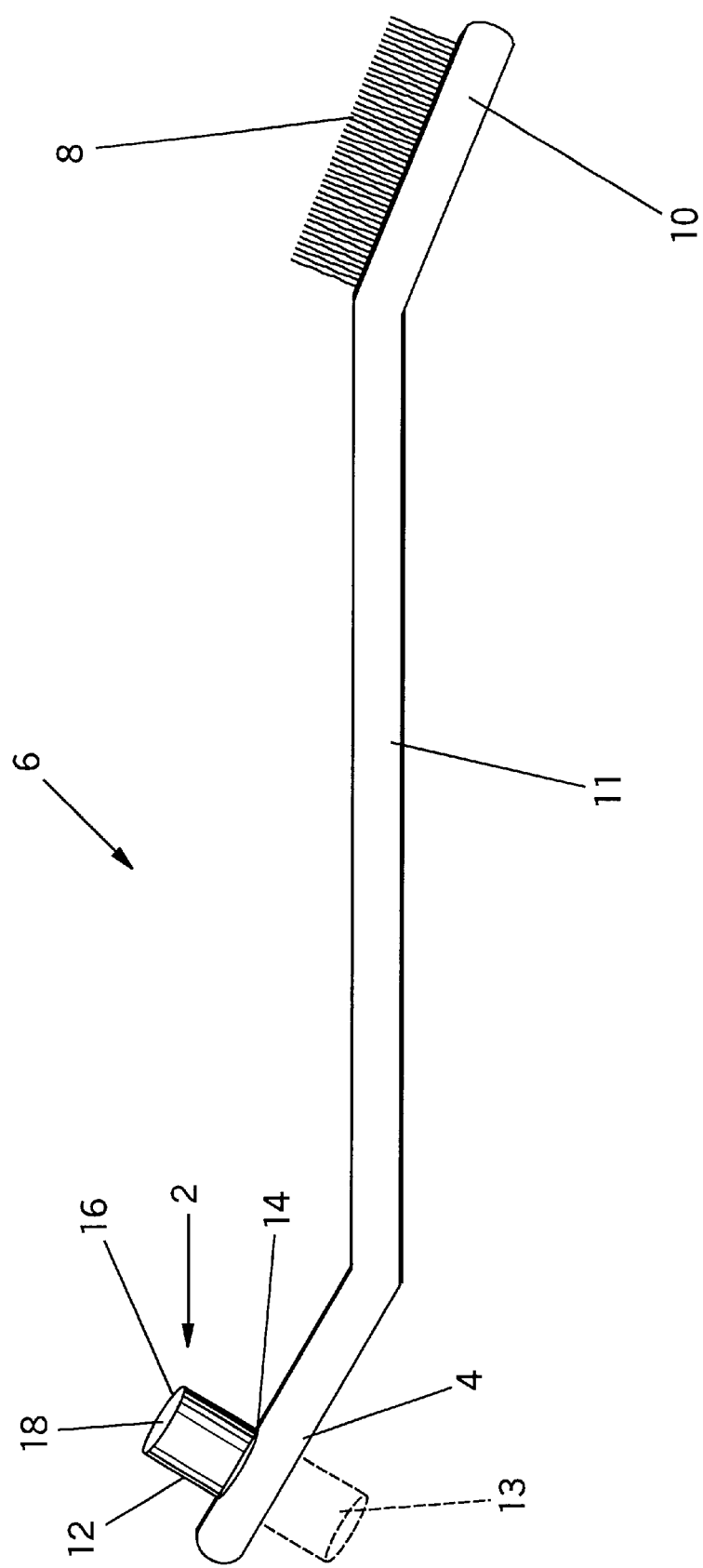
FIG. 1 is a side view of one embodiment of the applicator device of the present invention.

Preferably, the apparatus used to perform the method of the present invention is a cup-shaped rubber or plastic post or block, located on the handle of a toothbrush (see FIG. 1). In use, the desensitizing agent is applied to the recess in the top surface of the post so that pressing the applicator onto the tooth will cause the cup or block to flatten out, at least slightly, and seal the outside of the cup against the tooth surface, thereby through compression, partially pressuring the contents of the cup. This pressure and force created thereby drives the tubule blocking agent into the tubules against the outward flow in the tubule and overcomes the impediments created thereby. It also forces the desensitizing agents through or past any pre-existing organic material contained therein.

Referring now to FIG. 1, the preferred embodiment of the present invention comprises a cup-shaped rubber or plastic post or stud (2) attached to the distal end (4) of a conventional toothbrush (6) whose bristles (8) would be located at the proximal end (10) thereof. The cup-shaped post (2) is essentially cylindrical in shape comprised of a body portion (12), a base secured to the toothbrush (14) and a rim (16) surrounding the recessed indentation (18) for receiving the desensitizing composition. The applicator could conceivably be rectangular or polygonal in shape but a cylinder, square or rectangular-shaped post is simplest in terms of design and manufacture, and might also taper in slightly from the rim (16) to the base portion (14). The applicator may also be positioned as noted in phantom (13) on the other side of the handle (6) so as to be diametrically opposite that of the brush (8).

As shown in FIG. 1, the applicator is preferably attached to the distal end of a standard toothbrush and many angular variations of the handle are possible as evidenced by todays commercial brands. As seen here, the distal (4) and proximal (10) ends are positioned at angles equal but opposite to each other with respect to the main body of the handle (11). The handle and ends could also be linear if so desired. So long as sufficient room is allowed for the manual grasping of the toothbrush, any conceivable configuration is possible although that illustrated here is the simplest in terms of design and manufacture. The applicator post (2) could also be manufactured at the end of its own handle without the brush portion and used separately if desired.

Figures 2A, 2B:
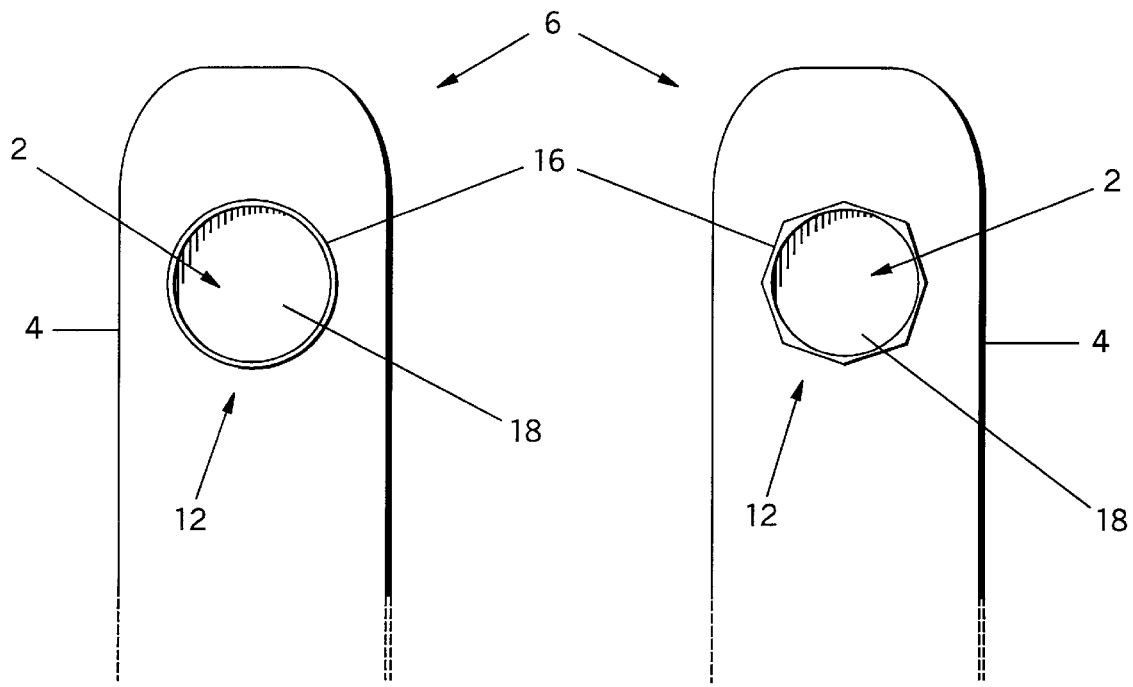
FIG. 2 is a top view of the applicator device of the present invention showing several possible embodiments.
Figure 2C:
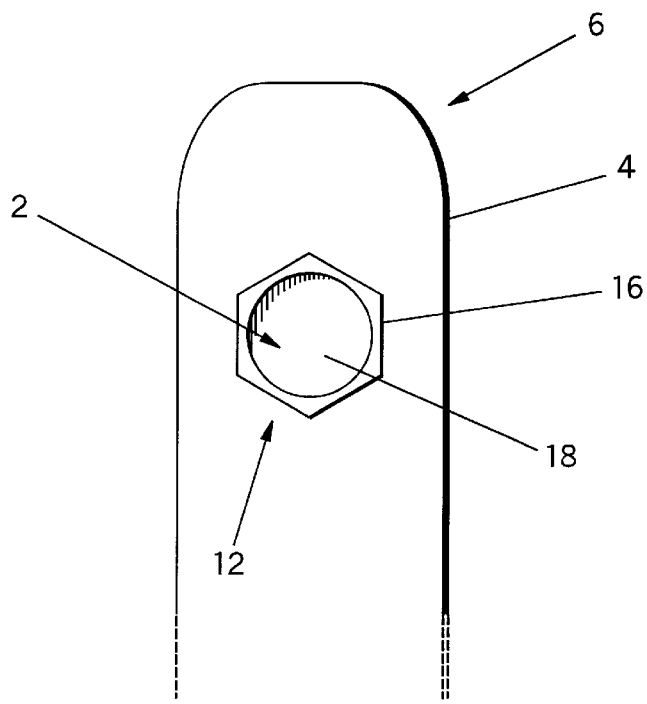
Figure 2D:
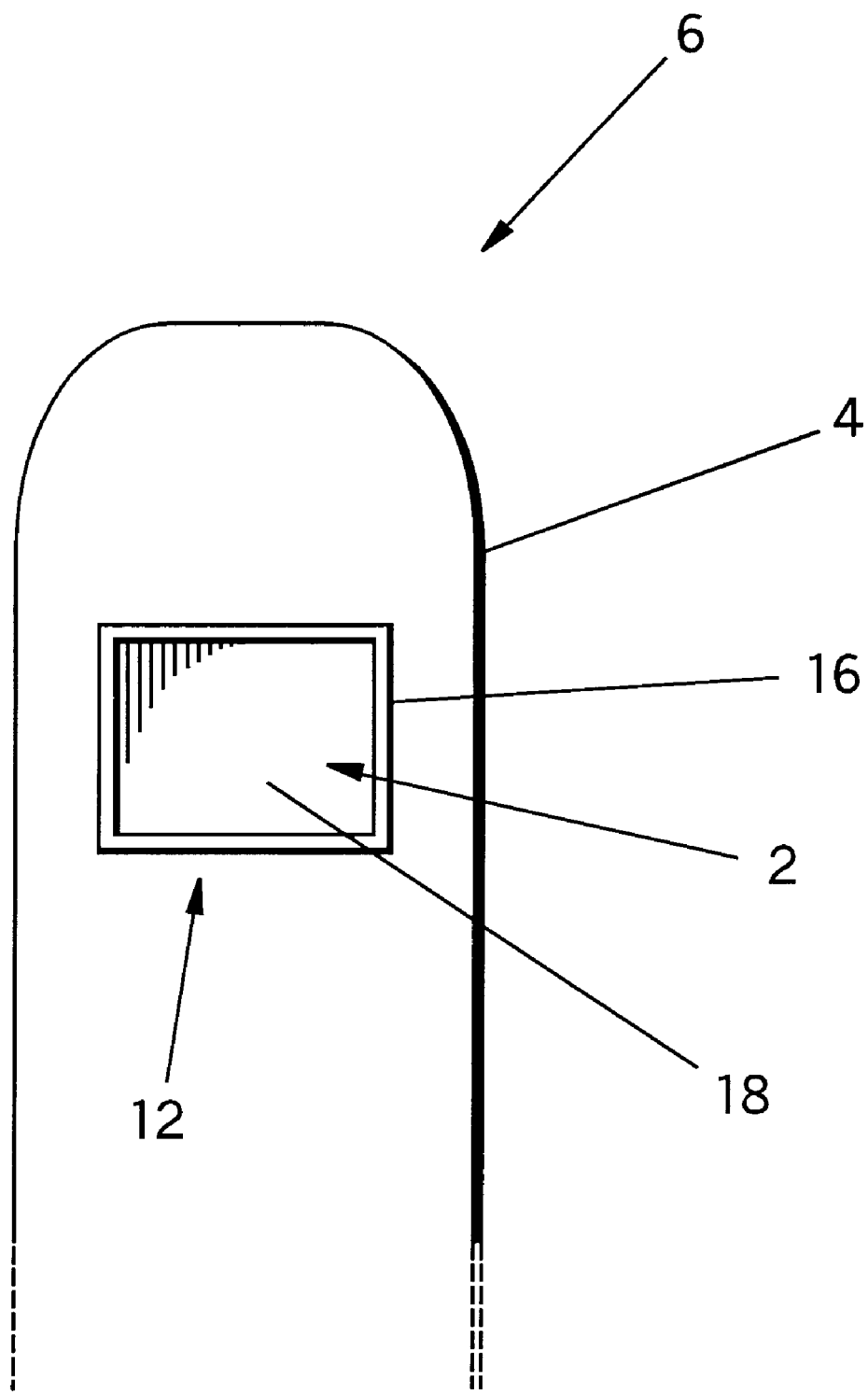

As shown in FIG. 2, four possible embodiments (a,b,c,d) as viewed from above show the applicator post (2) secured to the distal end (4) of the toothbrush (6). The applicator is preferably circular, square or rectangular in shape (a, d) with the recessed indentation (18) surrounded by a elevated rim portion (16) which defines the circumference of the cylindrical or rectangular shaped body (12) or may have a ridged or serrated surface (FIG. 3, 19) to receive the desensitizing material. The surface may also have a concavity (FIG. 3, 18). As before, instead of a circular rim (a) this could conceivably be rectangular or polygonal in shape (b,c) such as a pentagon or octagon. It could also be shaped in a bi-concave, i.e. "dumb-shaped" surface ovoid form (not shown). The cylindrical body with a circular rim is preferred however.

The circular rim (16) and recess (18) could also conceivably be omitted as the desensitizing agent can be applied directly to the tooth surface and then separately rubbed into the tubules with the applicator in the form of a cylindrical, square or rectangular rubber block with no recessed cup. Notwithstanding this, a cup is preferred and the thickness of the rim can also be varied (see b v. c) in order to alter the flexibility or stiffness of the cup as it is rubbed against the teeth.

Figure 3A:
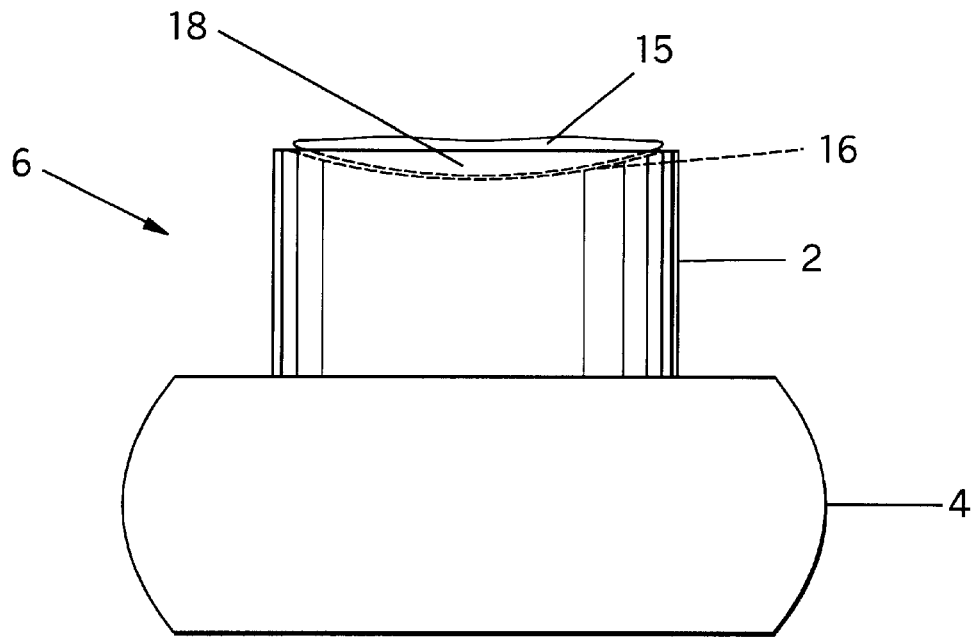
FIG. 3 is a cross-section of the applicator device in the cup and jagged surface embodiments.
Figure 3B:
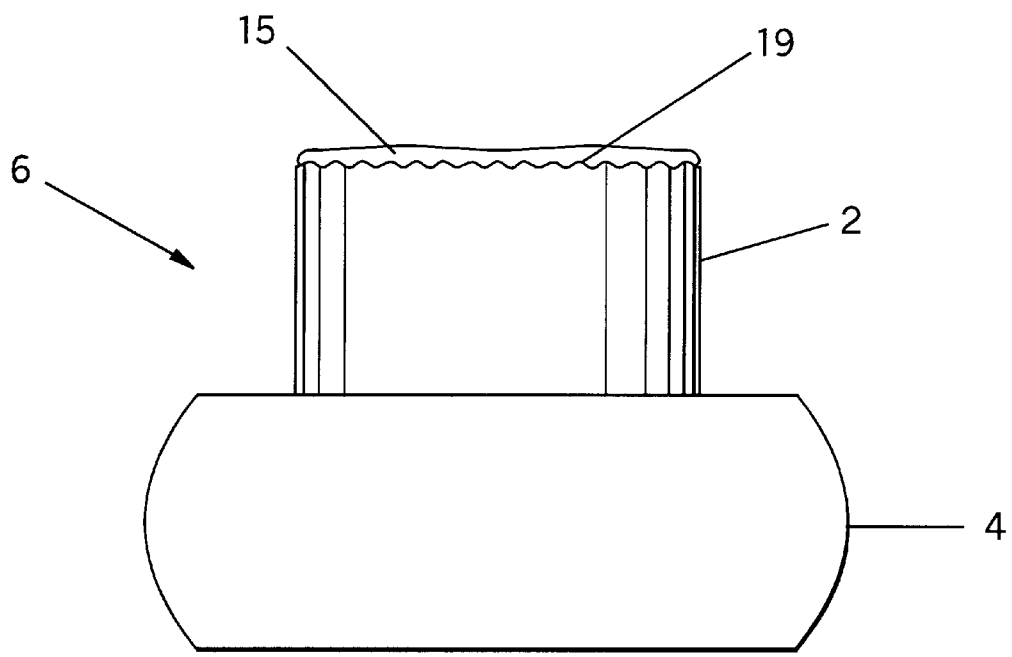

Referring now to FIG. 3, the present invention is shown in a cross-sectional perspective showing the cup-shaped (a) and serrated (b) surface embodiments. The desensitizing material (15) is placed within the recess of the applicator cup (18) or within the serrations (19) of the top surface of the block or post (2). The serrated edge of FIG. 3b may also be formed in a concave serrated embodiment, essentially the combination of FIGS. 3a and 3b, 36b. These surfaces then are the portion of the applicator which is pressed downward against the tooth surface forcing the desensitizing material into the dentinal tubules.

Figure 4:
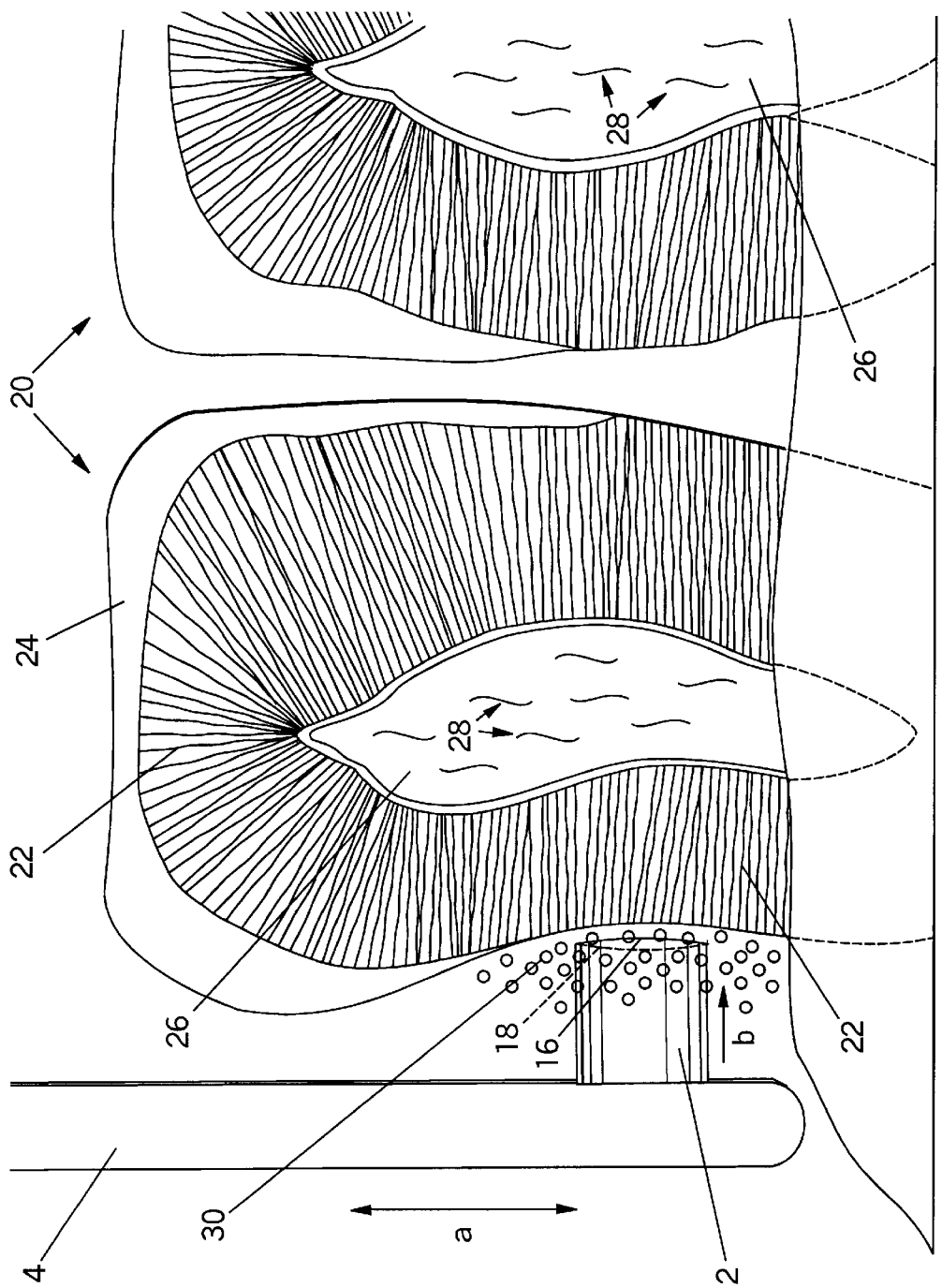
FIG. 4 is a magnified, cross-sectional view of the applicator in use applying a desensitizing composition to the tooth surface.

Referring now to FIG. 4, the applicator device (2) is shown in use according to the practice of the method of the present invention within the oral cavity. The cup-shaped device (2) is shown inverted and is flush against the surface of a tooth (20) in the region of the tooth neck. The tooth (20) is depicted as a cross-sectional view showing the dentinal tubules (22) below the enamel (24) and surrounding the pulp cavity (26) with its nerve tissue (28). The applicator contains the desensitizing agent (30) as represented by the many particles within the recess of the applicator (18), about the surface of the tooth (20) and within the tubules (22). In use, the distal end of the toothbrush handle (4) to which the cup (2) is attached is moved back and forth across the surface of the teeth (arrow a) while at the same time being pressed against the tooth (arrow b) to flatten the flexible rim (16) of the cup. This in turn forces the particles of the desensitizing composition (30) into the tubules (22) where they are blocked or the nerve "deadened" by an agent such as potassium nitrate. As depicted in FIG. 4, although most of the tubules are covered by enamel, in those afflicted by dentin sensitivity the dentin in the area of the tooth neck is frequently exposed. It is in these areas of exposed dentin that the tubules are open to the oral environment and it is here that the desensitizing agent is generally applied as shown.

The desensitizing agent useful in the practice of the present invention may be any of those known in the art such as oral compositions containing potassium nitrate, strontium chloride, strontium fluoride, potassium fluoride, polymeric particles, water soluble vinyl polymers, sodium citrate and mixtures thereof in a pharmaceutically acceptable carrier. Suitable polymeric particles useful as desensitizing agents include polymers or copolymers of monomers selected from the group consisting of acrylic acid, acrylamide, methyl methacrylate, alkylaminoalkyl acrylates, alkylaminoalkyl methacrylates, arylaminoalkyl acrylates, acylamino methacrylates, styrene, isoprene, butadiene, vinyl chloride, vinylidene chloride, ethylene, propylene, acrolein, tetrafluoroethylene, alkyl silicones, aryl silicones, vinyl toluene, and mixtures thereof. Some of these agents are commercially available in oral compositions such as Sensodyne® toothpaste and Carbopol® water soluble vinyl polymers are available from the B.F. Goodrich Company, Akron, Ohio as disclosed in U.S. Pat. No. 5,270,031 to Lim et. al. which is hereby incorporated by reference. These may be used alone or in combination as the consumer desires.

What I claim is:

1. A method for the desensitization of sensitive teeth comprising the forceful application of a desensitizing agent onto the surface of said teeth wherein said agent is disposed within a substantially cylindrical-shaped applicator comprising a recessed cup immovably attached to the distal end of a tooth brush at an angle of about 90°.

2. The method of claim 1 wherein said recessed cup is comprised of rubber.

3. The method of claim 1 wherein said recessed cup is comprised of plastic.

4. The method of claim 2 or 3 wherein said desensitizing agent relieves tooth hypersensitivity by blocking dentinal tubules in the teeth.

5. The method of claim 4 wherein said cup is serrated.

6. The method of claim 5 wherein said desensitizing agent is selected from the group consisting of potassium nitrate, strontium chloride, strontium fluoride, potassium fluoride, zinc nitrate, polymeric particles, water soluble vinyl polymers, sodium citrate and mixtures thereof in a pharmaceutically acceptable carrier.

7. The method of claim 6, wherein said polymeric particles are polymers or copolymers of monomers selected from the group consisting of acrylic acid, acrylamide, methyl methacrylate, alkylaminoalkyl acrylates, alkylaminoalkylmethacrylates, arylaminoalkylacrylates, acylamino methacrylates, styrene, isoprene, butadiene, vinyl chloride, vinylidene chloride, ethylene, propylene, acrolein, tetrafluoroethylene, alkyl silicones, aryl silicones, vinyl toluene, and mixtures thereof.

8. The method of claim 7, wherein said polymeric particles bear at least one functional group selected from the group consisting of aldehydic, carboxyl, sulfate, sulfonate, alkyl, aryl, haloalkyl, haloaryl, amino, alkylamino, acylamino, hydroxy, alkoxy, cyano, oximino, nitro, epoxy, amido, phosphate, phosphorate, and mixtures thereof.

9. The method of claim 8 wherein said desensitizing agent and carrier are formulated as a paste, gel or mouthwash composition.

10. The method of claim 9 wherein said polymers are selected from the group consisting of polyacrylic acid salts.

11. The method of claim 10 wherein said applicator comprises a polygonal-shaped post.

* * * * *